United States Patent [19]
Fraser

[11] 3,951,607
[45] Apr. 20, 1976

[54] GAS ANALYZER

[75] Inventor: Robert B. Fraser, Lagunitas, Calif.

[73] Assignee: Searle Cardio-Pulmonary Systems Inc., Emeryville, Calif.

[22] Filed: Nov. 29, 1974

[21] Appl. No.: 528,089

[52] U.S. Cl. .............................. 23/254 E; 250/226; 250/576; 313/217; 313/218; 356/178
[51] Int. Cl.² ................... G01J 3/50; G01N 21/26; G01N 33/16; H01I 5/16
[58] Field of Search........... 23/254 E, 254 R, 255 E, 23/255 R, 232 E, 232 R; 356/187, 178; 250/226, 564, 573, 575, 576; 313/218, 217 X

[56] References Cited
UNITED STATES PATENTS

| | | | |
|---|---|---|---|
| 2,574,655 | 11/1951 | Panofsky et al. | 313/218 X |
| 3,025,745 | 3/1962 | Liston | 23/255 E X |
| 3,209,197 | 9/1965 | Ahsmann et al. | 313/218 X |
| 3,229,566 | 1/1966 | Hutchinson et al. | 250/226 X |
| 3,312,853 | 4/1967 | Mela | 313/218 |
| 3,704,952 | 12/1972 | Bird | 356/187 X |

Primary Examiner—Robert M. Reese
Attorney, Agent, or Firm—Lothrop & West

[57] ABSTRACT

A gas analyzer especially for pulmonary use has a frame supporting a centrally mounted radiation chamber of about 10 to 30 millimeters (0.4 to 1.2 inches) substantially uniform inside diameter, having a circular-cylindrical glass wall closed by molybdenum protected aluminum ends connected in an electrical circuit to constitute an anode and a cathode. Leading from a patient's breathing tube is a conduit passing through a regulating valve and axially through the cathode, the conduit having an inside diameter of about 0.060 inches. The chamber is subjected to subatmospheric pressure through a duct of from about one-eighth to one-quarter inches inside diameter, passing through the anode to a vacuum pump. Arrayed equidistantly from the axis and around the chamber are several radiation detection devices, each connected to a display device. There are individual filters interposed between the chamber and at least some of the detecting devices.

4 Claims, 3 Drawing Figures

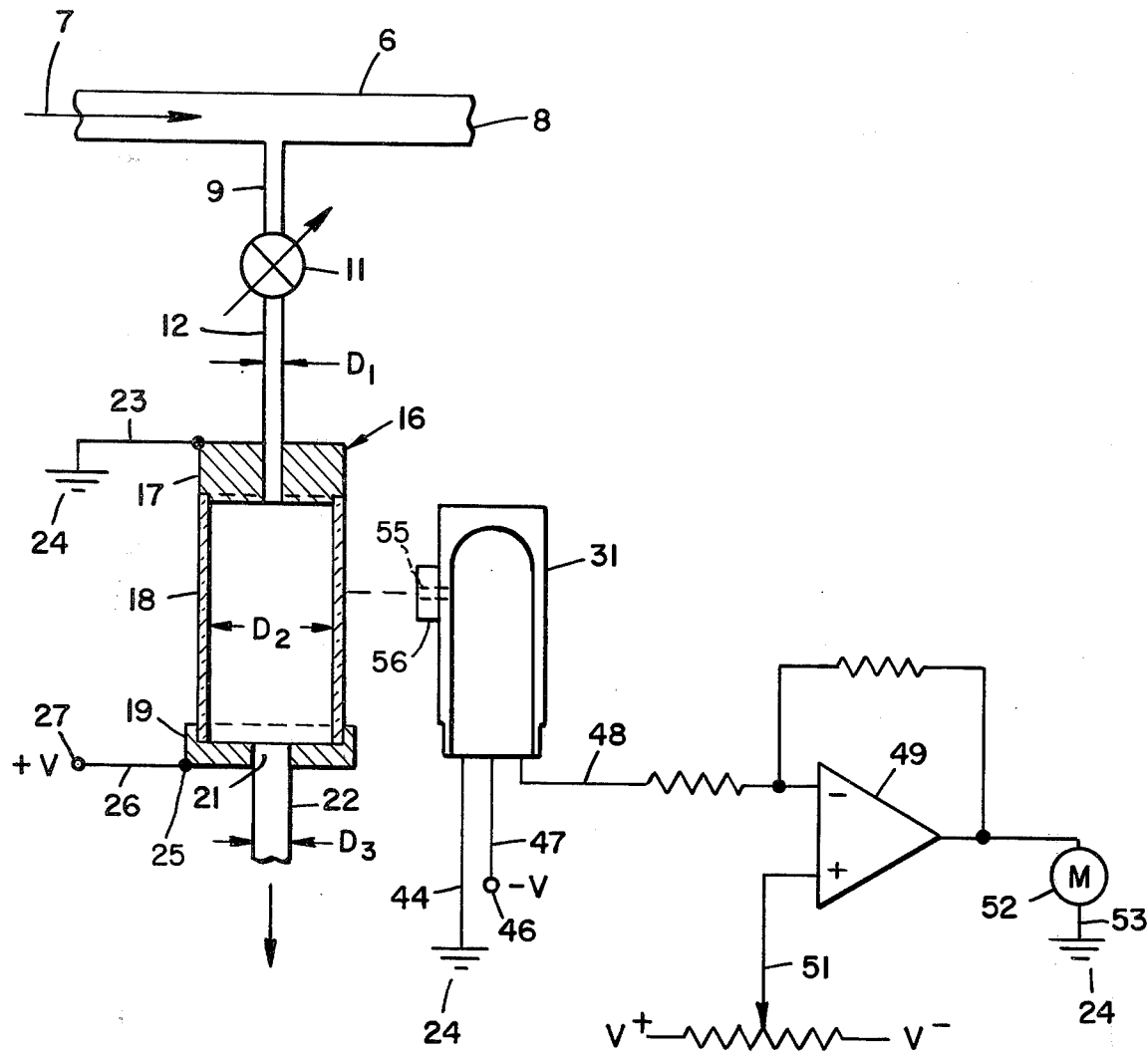
FIG_1

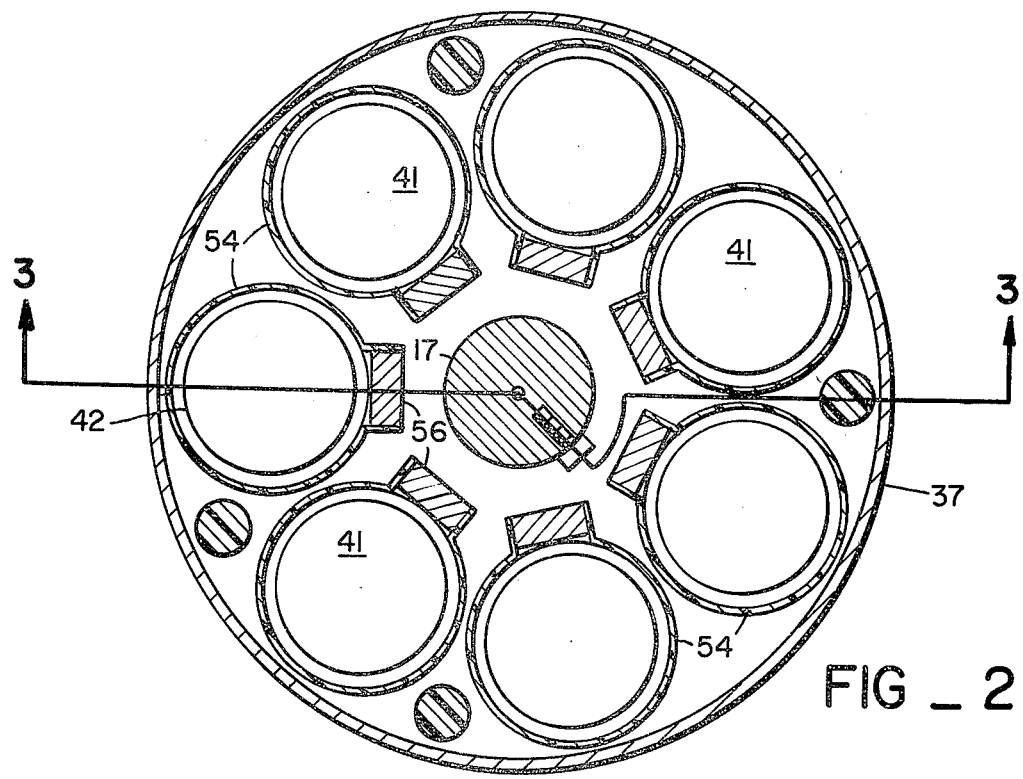
FIG_2
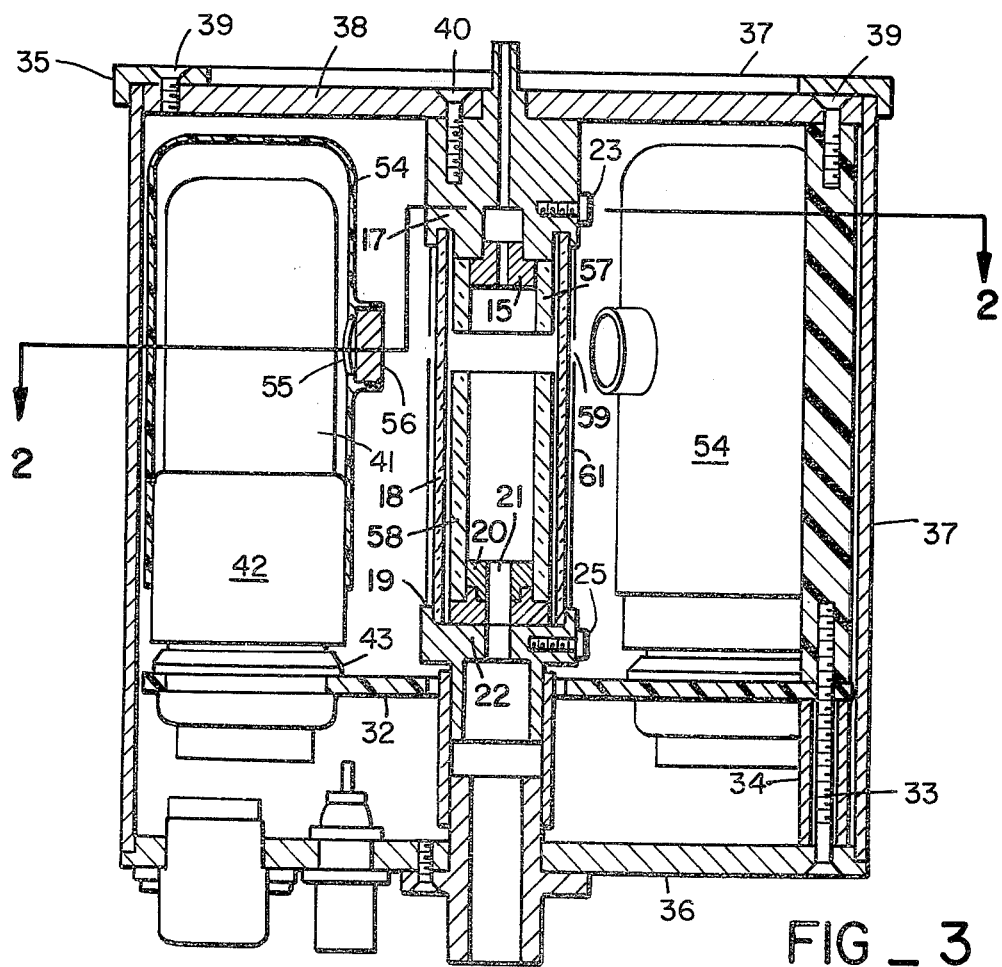
FIG_3

GAS ANALYZER

In the medical field there is an increasing need for a simple, portable, accurate and reliable means for determining one or more gas constituents of a patient's breath and for detecting relatively small amounts of physiological gases in a breathing tube connected to a patient. In some instances it is advisable to utilize a special single gas as a means for energizing or triggering the response of such a mechanism to others of the gases present, but preferably the arrangement utilizes no extra or carrier or trigger gas in order to afford an adequate indication.

There is a requirement for determining the presence of a moderate number of different gases exhaled by a patient into a breathing tube, perhaps five or six being the customary number of interest, although more or less can be detected when desired.

It is therefore an object of the invention to provide a gas analyzer that is sufficiently light and simple as to be portable, and which is sufficiently accurate and straightforward as to operate well over a protracted period under various different conditions of application and use.

Another object of the invention is to provide a gas analyzer which quickly furnishes a reliable indication of the presence in a patient's breath of any one or more of several different gases of physiological interest.

A further object of the invention is to provide a gas analyzer which can be utilized with or without an energizing gas.

An additional object of the invention is to provide a gas analyzer in which the various size or dimensional characteristics and preferred operating values are such as to produce a quick response time without sacrificing accuracy.

Another object of the invention is to provide a generally improved gas analyzer.

Other objects, together with the foregoing, are attained in the embodiment of the invention described in the accompanying description and illustrated in the accompanying drawings, in which:

FIG. 1 is a diagrammatic disclosure of one portion of a gas analyzer constructed pursuant to the invention and including the mechanical and electronic portions thereof;

FIG. 2 is a cross-section, not to scale, on horizontal planes represented by the line 2—2 of FIG. 3 showing a gas analyzer constructed pursuant to the invention; and FIG. 3 is a cross-section, the plane of which is indicated by the line 3—3 of FIG. 2.

While a gas analyzer pursuant to the invention can be incorporated in a large number of different ways, depending somewhat upon the extent and nature of the use of the device, it has with success been practically embodied in the form shown herein. In this form the device is intended to be utilized with a breathing tube 6 which at one end, the left end in FIG. 1, is connected to the customary fitting for accepting the patient's breath. On outflow or exhalation the travel is in the direction of the arrow 7 through the breathing tube 6 to a discharge point 8.

In order that the breath may be appropriately sampled, there is connected to the breathing tube 6 an inlet tube 9 leading through a manually controllable valve 11 into a conduit 12 of a particular configuration and size. The parts, in FIG. 1, have appropriate scale relationships. In one example for the use described, the conduit 12 preferably has an interior diameter $D_1$ of approximately 0.060 inches, plus or minus 0.020 inches. With this size of inlet conduit 12 the quantity and velocity of flow are sufficient to give adequate response time and to involve the transfer of a resonable amount of gas under the other conditions to be mentioned.

The inlet conduit 12 extends into an analyzing chamber 16. This is a special device including a massive head 17 or cover, preferably manufactured of aluminum or the like. The head 17 is provided with a graphite or molybdenum protector 15 pierced by an extension of the inlet conduit 12 to communicate with the interior of the chamber. The wall 18 of the chamber is generally circular-cylindrical in configuration and is made of glass. The wall is tightly sealed to the head 17 at one end, and at its other end is inserted into and is well sealed to a lower head 19, also of aluminum provided with a molybedenum or graphite protector. Through the head 19 and the protector there is an opening 21 in the communication with an outlet duct 22 leading to a source of subatmospheric pressure, such as a vacuum pump, not shown. It is important that the diameter $D_2$ of the chamber be approximately of a chosen value, and this conveniently is from 10 to 30 millimeters (0.4 to 1.2 inches) and, preferably, about 20 millimeters (0.8 inches) on the inside. Carrying out the size relationship, the inside diameter $D_3$ of the outlet duct 22 is conveniently about one-eighth inch to one-quarter inch. The point is that there should not be any undue restriction of gas flow, although flow from the interior chamber $D_2$ is limited to a controlled rate.

The chamber 16 is an analyzing chamber because the head 17 and protector 15 serve as a cathode in an electrical circuit, being joined by a conductor 23 to a ground connection 24 while the lower head 19 and protector 20 serve as a related anode, being connected by an anode bolt 25 and a conductor 26 to a source 27 of electromotive force. This is preferably a positive voltage about 600 volts above the ground 24. When this much of the mechanism is connected to the patient and to the vacuum pump and the valve 11 is opened to a chosen amount and the chamber is also electrically connected, then the gas flowing through the chamber is subject to a glow discharge. The various characteristics of the discharge depend upon the presence of the gas or gases therein. The discharge heats the cathode 17 but the cathode, being relatively massive and having substantial surface, acts to dissipate much of the imparted heat.

In this device, the valve 11 is preferably set at a flow rate of about 10 cc/min. as an optimum. The rate can be lowered to about 5 cc/min., but this affords a very slow response time. The flow rate can be increased to about 15 cc/min., but then the response tends to become markedly non-linear.

Arrayed around the chamber and equidistant from the vertical axis thereof are several detecting devices 31 (FIGS. 2 and 3). Each of these is mounted on a plate 32 forming part of the frame structure of the device. The plate 32 is preferably secured by bolts 33 extending through spacers 34 to the base plate 36 of the frame. The detecting devices 31 are housed and protected by a frame shell 37 resting on the base plate 36. A removable cap has a flange ring 35 secured by appropriate screws 39 and itself is held to the cathode 17 be screws 40.

Each of the detecting devices 31, there being seven in the present embodiment, is inclusive of a photomultiplier tube 41 of the usual sort, having a base 42 received by a receptacle 43 on the plate 32. Each tube 41 is connected in an appropriate circuit (FIG. 1). The circuit includes a lead 44 extending to the ground 24. A source 46 of negative voltage is joined to the tube through a lead 47. A conductor 48 from the photomultiplier tube 41 goes through an amplifier 49 having an appropriate adjustment 51 thereon to eliminate output offset voltage from the amplifier. The amplifier supplies an output meter 52 connected through a conductor 53 to ground 24.

Each of the photomultiplier tubes is surrounded by a radiation opaque shield 54 designed to fit slidably on the base 42. There is an aperture 55 or orifice at one point in the shield side wall. The orifice is approximately one-quarter inch in diameter and permits radiation traveling through the wall 18 of the analyzing chamber 16 to encounter a filter 56. Each filter is unique and is particularly designed to pass only the spectrum of a particular gas. In this way the spectra of seven different gases are individually detectable in one analyzing unit.

The filter 56 is properly positioned with respect to the analyzing chamber and the photomultiplier tube 41 by axial movement and by rotation of the shield 54. That is, the shield can be manually rotated, lifted and lowered until the emanation from the chamber through the filter is properly directed upon the otherwise encased photomultiplier tube. The radiation from the chamber is simultaneously transmitted to the seven receptors, each of which has its own indicating circuit, as described. Each tube 41 can serially be connected to the meter 52, thus to afford readings of the output due to each one of up to seven different gases to be detected. Also continuous monitoring of each of the seven gases can be done simultaneously by an outside indicating or recording instrument.

In a device of the nature described, the delay time in indicating results if of the order of 50 to 100 milliseconds so that the device can properly be used to give "on line" continuous readings.

In many instances, in fact in early work with the analyzer, it was customary to operate the unit with a current of helium gas through the analyzing chamber, the helium gas acting as an exciter for the other gas or gases present. By appropriate means, the helium value was subtracted from the composite result to yield a value for each particular other gas being monitored. This afforded a simple and accurate detection means for any of a number of anesthetic, physiological and test gases. The earlier technique was based on the use of a carrier gas, such as helium, and depended largely upon the use of excited helium metastable atoms as exciters for other gases. It has more recently been found that by making the detecting device sustantially as shown herewith with the dimensions and relationships as indicated and described, helium or another carrier gas is not needed. It is not necessary to use metastable helium or comparable ions for excitation. Individual gases alone or mixed can be separately detected. Helium itself, instead of being utilized simply as a carrier or exciter, can also serve as a gas for physiological exploration or detection.

It has been found in protracted operation that sometimes there are difficulties due to electrode sputtering and due to deposits of metal oxides in the analyzing chamber. The oxidation has been substantially reduced by employing molybdenum as the exposed metal for the anode and the cathode or in the form of the protectors 15 and 20 augmenting the anode and cathode. Molybdenum is advantageous since molybedenum oxide, under conditions of chamber operation, is in gas form and exhausts with the gas or gases being analyzed and without deposit. The electrical sputtering otherwise encountered is substantially reduced by the use of cylindrical glass of ceramic insulation such as 57 and 58 within the outer glass wall 18 and extending from the ends to an annular gap in the region of the apertures 55. The sputtered particles from the cathode 15 then encounter the glass or ceramic insulation leaving the outer glass wall 18 clean. The insulators are relatively thick radially relative to the axial gap so they have a substantial collimating effect upon the radiation from the discharge. The radiation is shielded from errant rays and further collimated by passing through relatively small apertures 59 in a thin light shield 61 of opaque material surrounding the glass wall 18.

In the operation of the structure, the breathing tube 6 is connected to the patient as described, the circuitry is energized, and the meter 52 is connected serially or as desired to whatever ones of the various detecting devices 41 are appropriate to afford a spectographic reading of the invididual gases. These, for example, are nitrogen, oxygen, carbon dioxide, carbon monoxide, helium, acetylene, nitrous oxide, nitric oxide, sulphur dioxide and some of the anesthetic gases.

What is claimed is:

1. A gas analyzer especially for pulmonary use comprising: a patient's breathing tube, a cylindrical analyzing chamber of insulating material having electrical conductive ends and being of substantially uniform internal diameter of from 0.4 to 1.2 inches between said ends, means including a conduit of a diameter of from 0.04 to 0.08 inches extending axially through one of said ends and connecting said chamber to said tube, means including a duct of a diameter of from 0.125 to 0.25 inches extending axially through the other of said ends for connecting said chamber to subatmospheric pressure and to thereby draw gases from said tube through said chamber, means for applying to said ends of said chamber a voltage difference to cause radiation from gas in said chamber, a plurality of radiation detection devices arrayed around said chamber, radiation filters between said chamber and at least some of said detection devices, each radiation filter being for a particular one of a plurality of gases in said chamber, and means for displaying the response of each of said detection devices.

2. A gas analyzer as in claim 1 in which said applying means includes an axially perforate cathode and an axially perforate anode respectively interposed between said conduit and said duct.

3. A gas analyzer as in claim 1 including a radiation opaque shield around said chamber, said shield having a radiation orifice therein for passing radiation from said chamber to one of said filters.

4. A gas analyzer as in claim 3 in which said shield is slidable on said chamber.

* * * * *